United States Patent [19]

Hammerschmidt et al.

[11] 4,426,333
[45] Jan. 17, 1984

[54] PROCESS FOR THE PREPARATION OF 1-BENZOYLAMINO-8-HYDROXYNAPH-THALENE-4,6-DISULPHONIC ACID (BENZOYL-K ACID)

[75] Inventors: Erich Hammerschmidt, Bergisch Gladbach; Horst Behre, Odenthal; Bruno Krüger, Cologne; Adolf Winkler, Leverkusen, all of Fed. Rep. of Germany

[73] Assignee: Bayer Aktiengesellschaft, Leverkusen, Fed. Rep. of Germany

[21] Appl. No.: 371,386

[22] Filed: Apr. 23, 1982

[30] Foreign Application Priority Data

May 13, 1981 [DE] Fed. Rep. of Germany ....... 3118903

[51] Int. Cl.$^3$ ........................................... C07C 143/42
[52] U.S. Cl. ................................................ 260/507 R
[58] Field of Search ................................... 260/507 R

[56] References Cited

FOREIGN PATENT DOCUMENTS 9743 9/1979 European Pat. Off. ............ 260/509

Primary Examiner—Nicky Chan
Attorney, Agent, or Firm—Sprung, Horn, Kramer & Woods

[57] ABSTRACT

The invention relates to a process for the preparation of 1-benzoylamino-8-hydroxynaphthalene-4,6-disulphonic acid (benzoyl-K acid) by reacting 1-amino-8-hydroxynaphthalene-4,6-disulphonic acid (K acid) with benzoylating agents, according to which process mixtures of aminonaphtholdisulphonic acid isomers are used instead of pure K acid, which mixtures contain over 40% by weight of K acid, relative to the total amount of diazotizable compounds in the mixture of isomers, and in which no other single isomer has a proportion which exceeds 10% by weight of the total amount of diazotizable compounds in the mixture of isomers.

10 Claims, No Drawings

PROCESS FOR THE PREPARATION OF 1-BENZOYLAMINO-8-HYDROXYNAPHTHALENE-4,6-DISULPHONIC ACID (BENZOYL-K ACID)

The invention relates to an improved process for the preparation of 1-benzoylamino-8-hydroxynaphthalene-4,6-disulphonic acid (benzoyl-K acid) in the form of its alkali metal salts.

Benzoyl-K acid is an important intermediate product in the preparation of dyestuffs (see Ullmanns Enzyklopädie der technischen Chemie [Ullmann's Encyclopaedia of Industrial Chemistry], 4th Edition, Volume 17, page 107). Benzoyl-K acid (as a dialkali metal salt) has hitherto been prepared by reacting 1-amino-8-naphthol-4,6-disulphonic acid (K acid) at 35° to 40° C. in a solution containing sodium hydroxide with benzoyl chloride, splitting the O-benzoyl compound formed in the reaction by heating the reaction mixture at 90° C. and subsequently precipitating benzoyl-K acid by acidifying the reaction mixture (see Ullmanns Enzyklopädie der technischen Chemie [Ullmann's Encyclopaedia of Industrial Chemistry], loc. cit.). This process has the disadvantage that pure K acid is required as a starting compound. Pure K acid is obtainable only in poor yields, because considerable losses of K acid occur when separating and isolating K acid from reaction mixtures containing K acid and in the subsequent purification of the isolated K acid.

It has now been found that it is not necessary to use pure K acid for the preparation of benzoyl-K acid, but that benzoyl-K acid can be prepared in unchanged purity but in a considerably improved yield (relative to melanic acid or naphthalene), if mixtures of aminonaphtholdisulphonic acid isomers containing K acid are benzoylated instead of pure K acid. It has in fact been found, surprisingly, that the other isomers contained in these mixtures do not hinder the precipitation of benzoyl-K acid, if no single isomer—with the exception of K acid—has a proportion which exceeds 10% by weight of the total mixture of isomers, regardless of the total number of isomers contained in the mixture.

The invention therefore relates to a process for the preparation of benzoyl-K acid by reacting K acid with benzoylating agents, which is characterised in that mixtures of aminonaphtholdisulphonic acid isomers are used instead of pure K acid, which mixtures contain over 40% to 90% by weight of K acid, relative to the total amount of diazotisable compounds in the mixture of isomers, on the basis of a molecular weight of 319, and in which no other single isomer has a proportion which exceeds 10% by weight of the total amount of diazotisable compounds in the mixture of isomers.

Mixtures of aminonaphtholdisulphonic acid isomers, to be used according to the invention, preferably contain 50 to 90% by weight of K acid, relative to the total amount of diazotisable compounds in the mixtures of isomers, on the basis of a molecular weight of 319. Particularly preferable mixtures of aminonaphtholdisulphonic acid isomers contain 55 to 75% by weight of K acid, 0 to 10% by weight of H acid and 2 to 10% by weight of iso-K acid (% by weight relative to the total amount of diazotisable compounds in the mixture of isomers, on the basis of a molecular weight of 319).

Mixtures of aminonaphtholdisulphonic acid isomers, to be used according to the invention, can contain, in addition to K acid and other aminonaphtholdisulphonic acid isomers, for example H acid and iso-K acid, by-products, decomposition products or unreacted starting products from process stages (sulphonation, nitration and reduction) preceding the alkaline hydrolysis under pressure of aminonaphthalenetrisulphonic acid mixtures, provided that no single compound having amino groups has a proportion which exceeds 10% by weight of the total amount of diazotisable compounds in the mixture of isomers. Examples which may be mentioned of by-products, decomposition products and unreacted starting products are naphthalene-di-, -tri- and -tetrasulphonic acids, nitronaphthalene-mono-, -di- and -trisulphonic acids, naphthylamine-mono-, -di- and -tri-sulphonic acids, for example 1-aminonaphthalene-4,6- and -4,8-disulphonic acid and 2-aminonaphthalene-4,8-disulphonic acid, naphthol-mono- and -di-sulphonic acids, dihydroxynaphthalene-mono- and -di-sulphonic acids, and also dinaphthylsulphonesulphonic acids and their amino, nitro and hydroxy derivatives, and also oxidation products of naphthalene and/or of naphthalenesulphonic acids.

These mixtures of aminonaphtholdisulphonic acid isomers which may also contain by-products, decomposition products or starting products from preceding process stages and which are to be employed according to the invention, are obtained, for example, in the alkaline hydrolysis under pressure of 1-naphthylamine-4,6,8-trisulphonic acid (melanic acid) or of mixtures of melanic acid isomers (mixtures of melanic acid isomers = mixtures of naphthylaminetrisulphonic acid isomers which contain at least 40% by weight, preferably 45 to 75% by weight, of melanic acid, relative to the total amount of diazotisable compounds in the mixture of isomers, on the basis of a molecular weight of 319. The preparation of mixtures of melanic acid isomers has been described, for example, in FIAT Final Report, No. 1016, pages 42–44).

If hydrolysis mixtures obtained in an alkaline hydrolysis under pressure of mixtures of melanic acid isomers contain more than 10% by weight of 1-amino-8-hydroxynaphthalene-3,6-disulphonic acid (H acid), relative to the total amount of diazotisable compounds in the hydrolysis mixture, H acid, as a monoalkali metal salt, is precipitated and separated from these alkaline hydrolysis mixtures before they are employed in the benzoylation, by acidifying them to have a pH value of 0 to 4, preferably 0.5 to 2.5, and, if appropriate, by diluting with water. (This separation has been described in German Offenlegungsschrift No. 2,843,680).

Mixtures of aminonaphtholdisulphonic acid isomers, to be employed according to the invention, are benzoylated in aqueous solution or suspension. The benzoylation can be carried out at pH values of 3 to 10. The pH value of aqueous solutions or suspensions to be benzoylated is preferably 7 to 10, in particular 8 to 9. To establish and maintain the pH value alkali metal hydroxides or alkali metal carbonates are customarily used, in a solid form or in the form of aqueous solutions. Sodium carbonate or sodium hydroxide are preferably employed.

To benzoylate mixtures of aminonaphtholdisulphonic acid isomers, to be employed according to the invention, all compounds which are suitable for N-benzoylation can be used. Preferred benzoylating agents are benzoic anhydride and benzoyl halides; benzoyl chloride is preferably used. The benzoylating agent is preferably employed in a quantity which is such that 1.0 to 1.7 mols, preferably 1.1 to 1.4 mols, of benzoylating agent are used per 1 mol of diazotisable compound in the mixtures of aminonaphtholdisulphonic acid isomers.

The reaction, according to the invention, of mixtures of aminonaphtholdisulphonic acid isomers with a benzoylating agent is carried out at temperatures of 10° to 100° C., preferably 25° to 75° C. The splitting of the O-benzoyl compound is carried out within the same temperature ranges, preferably at temperatures of 40° to 95° C.

The reaction time depends essentially on the reaction temperature and on the pH value during the reaction. Increasing temperature and increasing pH value of the reaction mixture shorten especially the time required for splitting the O-benzoyl compound.

Benzoyl-K acid is advantageously precipitated in the form of its alkali metal salts at pH values <7, preferably at pH values of 3 to 6 and in particular 4 to 5. The precipitation can be improved by maintaining certain alkali metal ion concentrations in the benzoylating mixture. These alkali metal ion concentrations are about 2 to 5 g equivalents/l of benzoylating mixture. If benzoylating mixtures do not already contain the desired amounts of alkali metal ions, the alkali metal ion concentrations desired are established by the addition of alkali metal salts which are soluble in the benzoylating mixture, preferably sodium salts, such as sodium chloride or sodium sulphate.

Benzoyl-K acid (as an alkali metal salt) is separated from the benzoylating mixture at temperatures below 60° C., usually 0° to 60° C., preferably at temperatures of 15° to 45° C. After the product has been separated off (filtered off or centrifuged off) it is washed with alkali metal salt solutions and then dried, if appropriate in vacuo. It is possible to achieve, by adapting alkali metal ion concentrations, pH value and isolation temperature, that only the alkali metal salt of benzoyl-K acid precipitates from the benzoylating mixture, whilst other compounds contained in the benzoylating mixture remain in solution.

Benzoyl-K acid is obtained, by the process according to the invention, in a high yield, relative to the K acid content in the mixtures of aminonaphtholdisulphonic acid isomers to be used according to the invention, and in excellent purity. The reason this is surprising is that there are a large number of chemically very similar compounds present in the mixtures of aminonaphtholdisulphonic acid isomers to be used as starting compounds according to the invention which form, in an identical manner to that of K acid, benzoyl derivatives which closely approach those of benzoyl-K acid in their physical and chemical properties. It was therefore to be expected that it would be impossible to separate benzoyl-K acid from such benzoylating mixtures in a pure form and, in addition, in high yields.

Compared to the known benzoylation of pure K acid, the process according to the invention offers considerable advantages. Since the process stages in which K acid is precipitated, isolated and purified are omitted in the process according to the invention, the K acid produced in an alkaline hydrolysis under pressure is completely utilised in the benzoylation and an improved yield of benzoyl-K acid, relative to melanic acid employed or to originally employed naphthalene, is thus achieved. Compared to previously achieved yields of benzoyl-K acid, a relative yield increase of 8 to 14% is achieved. In addition, the process according to the invention produces a reduced loading of effluent with organic carbon. Furthermore, dispensing with the K acid isolation reduces the consumption of salt and acid for the separation and hence the quantity of corresponding compounds in the effluent by more than half compared with the known processes.

EXAMPLE 1

The pH of 600 ml of an alkaline K acid solution (obtained by alkaline hydrolysis under pressure of melanic acid; content of diazotisable compounds: 0.4 mol; content of K acid: 0.34 mol) is adjusted by the addition of 30% strength hydrochloric acid to a value of 8.8 and the solution is diluted at the same time with water to a total volume of 830 ml. 67.5 g (0.48 mol) of benzoyl chloride are added at 25° to 45° C. in the course of 2 hours to this solution, the pH value of which is maintained by the simultaneous addition of about 10 ml of a 50% strength sodium hydroxide solution at 8.4 to 8.8. The reaction mixture is stirred for 2 hours at 40° to 45° C. while the pH value is being maintained, then adjusted by means of sodium hydroxide solution to a pH value of 9.5 and heated for 1.5 hours at 90° to 95° C. while this pH value is being maintained.

The reaction mixture is then diluted with water to a volume of 1,700 ml and adjusted at 80° to 90° C. by means of about 20 ml of 30% strength hydrochloric acid to a pH value of 6 and then with 30 ml of acetic acid to a pH value of 5. On slowly cooling the mixture down to 20° C. benzoyl-K acid precipitates. It is filtered off with suction and washed 2 times with 100 ml each of a semi-saturated sodium chloride solution.

The composition of the moist product filtered off is determined by thin layer chromatography. The yield of pure (100% pure) benzoyl-K acid is 137 g (=95% of theory, relative to K acid contained in the alkaline hydrolysis solution or 79.5%, relative to melanic acid employed in the hydrolysis under pressure). The benzoyl-K acid isolated is free of H acid, K acid and iso-K acid (1-amino-6-hydroxynaphthalene-4,8-disulphonic acid).

If instead of an alkaline K acid solution an amount of pure K acid which is equivalent to the K acid content of the solution is benzoylated, the yield of benzoyl-K acid is only 72% of theory, relative to melanic acid (used in the preparation of the K acid).

EXAMPLE 2

2,504 g of a solution of a mixture of aminonaphtholdisulphonic acid isomers were used. This solution was obtained by alkaline hydrolysis under pressure of a mixture of melanic acid isomers and subsequent separation of the H acid which was precipitated by acidifying the alkaline hydrolysis mixture. Content in the solution of: diazotisable compounds 0.4 mol, K acid 0.27 mol, H acid 0.02 mol and iso-K acid 0.02 mol.

The solution contains not only K acid, H acid and iso-K acid but also a large number of quantitatively indeterminable amounts of by-products, decomposition products and oxidation products which have been produced by trisulphonation of naphthalene, subsequent nitration, reduction and alkaline hydrolysis under pressure. The pH of the solution is adjusted by the addition of sodium hydroxide solution to a value of 8.8. 67.5 g (0.48 mol) of benzoyl chloride are added at 20° C. to the solution while a pH value of 8.4 to 8.8 is being maintained. The reaction mixture, with the pH value being maintained, is first stirred for 2 hours at 45° C. and then for 2 hours at 70° C. A sodium ion concentration of 3.7 g equivalents/l is then established in the reaction solution by the addition of sodium sulphate. Benzoyl-K acid is then precipitated by lowering the pH of the reaction mixture to a value of 4.5 to 5.0 by means of (44 ml) 50% strength sulphuric acid and slow cooling down to 40° C. The precipitate is filtered off with suction and washed 2 times with 100 ml each of a semi-saturated sodium sulphate solution and then dried for 24 hours at 80° C. in vacuo (270 mbar).

The yield of 100% strength benzoyl-K acid is 109 g (=95% of theory, relative to the K acid in the solution of the mixture of isomers, or 40%, relative to naphthalene).

The composition of the benzoyl-K acid is determined by high pressure liquid chromatography; the following values were found:

disodium salt of benzoyl-K acid: 85.1% by weight
benzoyl-H acid: 0% by weight
K acid: 0% by weight
H acid: 0% by weight
iso-K acid: 0% by weight
benzoic acid: 0% by weight
water: 3.1% by weight
sodium chloride: 0.2% by weight
sodium sulphate: 11.6% by weight

What is claimed is:

1. In the process for the preparation of 1-benzoylamino-8-hydroxynaphthalene-4,6-disulphonic acid (benzoyl-K acid) by reacting 1-amino-8-hydroxynaphthalene-4,6-disulphonic acid (K acid) with benzoylating agents and isolating the benzoyl-K acid in the form of its alkali metal salt, the improvement which comprises using instead of pure K acid a mixture of aminonaphtholdisulphonic acid isomers which contains over 40% to 90% by weight of K acid, relative to the total amount of diazotisable compounds in the mixture of isomers, on the basis of a molecular weight of 319, and in which mixture no other single isomer has a proportion which exceeds 10% by weight of the total amount of diazotisable compounds in this mixture.

2. The process of claim 1, wherein a mixture of aminonaphtholdisulphonic acid isomers is used, which contains 50 to 90% by weight of K acid, relative to the total amount of diazotisable compounds in the mixture of isomers, on the basis of a molecular weight of 319.

3. The process of claim 1, wherein a mixture of aminonaphtholdisulphonic acid isomers is used, which contains 55 to 75% by weight of K acid, 0 to 10% by weight of H acid and 2 to 10% by weight of iso-K acid, % by weight being relative to the total amount of diazotisable compounds in the mixture of isomers.

4. The process according to claim 1, wherein a mixture of aminonaphtholdisulphonic acid isomers is used which is obtained in the alkaline hydrolysis under pressure of 1-naphthylamine-4,6,8-trisulphonic acid (melanic acid) or of a mixture of melanic acid isomers.

5. The process of claim 1, wherein 1.0 to 1.7 mols of benzoylating agent are used per 1 mol of diazotisable compound in the mixture of aminonaphtholdisulphonic acid isomers.

6. The process of claim 1, wherein 1.1 to 1.4 mols of benzoylating agent are used per 1 mol of diazotisable compound in the mixture of aminonaphtholdisulphonic acid isomers.

7. The process of claim 1, wherein the benzoyl-K acid is precipitated at a pH value of 3 to 6.

8. The process of claim 1, wherein the isolation of benzoyl-K acid is carried out at a temperature of 0° to 60° C.

9. The process of claim 1, wherein the benzoyl-K acid is precipitated from a benzoylating mixture the alkali metal ion concentration of which amounts to 2 to 5 g equivalents per liter of benzoylating mixture.

10. The process according to claim 4 wherein the H acid present in the mixture of melanic acid isomers has been precipitated by acidification and removed from said mixture.

* * * * *